(12) United States Patent
Graczyk et al.

(10) Patent No.: US 7,291,630 B2
(45) Date of Patent: Nov. 6, 2007

(54) AZAINDOLES AS INHIBITORS OF C-JUN N-TERMINAL KINASES

(75) Inventors: Piotr Graczyk, London (GB); Hirotoshi Numata, London (GB); Gurpreet Bhatia, London (GB); Darren Peter Medland, London (GB)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/509,127

(22) PCT Filed: Mar. 17, 2003

(86) PCT No.: PCT/GB03/01115

§ 371 (c)(1),
(2), (4) Date: Aug. 26, 2005

(87) PCT Pub. No.: WO03/082869

PCT Pub. Date: Oct. 9, 2003

(65) Prior Publication Data

US 2006/0111390 A1 May 25, 2006

(30) Foreign Application Priority Data

Mar. 28, 2002 (GB) .................. 0207488.8
Jan. 8, 2003 (GB) .................. 0300400.9

(51) Int. Cl.
*A61K 31/437* (2006.01)
*C07D 471/04* (2006.01)
(52) U.S. Cl. ..................... 514/300; 546/113
(58) Field of Classification Search ................ 546/113; 514/300
See application file for complete search history.

(56) References Cited

U.S. PATENT DOCUMENTS 6,642,375 B2 * 11/2003 Inomata et al. ............ 536/26.6

FOREIGN PATENT DOCUMENTS

EP 0737685 A1 10/1996

(Continued)

OTHER PUBLICATIONS

CAS Accession No. 2001:432896, Registry No. 344454-31-1.*
CAS Document No. 135:43132.*
West, Anthony R., Solid State Chemistry and its Applications (Wiley, New York, 1988).*
Bundgaard, Design of Prodrugs (Elsevier Science Publishers 1985).*
Smulik and Diver, Synthesis of Cyclosporin A-Derived Affinity Reagents by Olefin Metathesis, Organic Letters, 4(12):2051-2054 (2002).*

LeConte, Reach-Through Claims, International Pharmaceutical (2002) (also available at <http://www.bakerbotts.com/infocenter/publications/detail.aspx?id=bffe4a7d-5beb-dcf8-a189-15a5f190f0eb>).*
Silva, Reach Through Claims: Bust or Boon?, Intellectual Property Update (available at: <http://www.dorsey.com/publications/legal_detail.aspx?FlashNavID=pubs_legal&pubid=170565003>).*
Vippagunta et al., Crystalline Solids, Advanced Drug Delivery Reviews, 48(1): 3-26 (2001).*
CAS Document No. 135:107148.*
Cao, J. et al., "Distinct Requirements for p38α and c-Jun N-terminal Kinase Stress-activated Protein Kinases in Difference Forms of Apoptotic Neuronal Death." *The Journal of Biological Chemistry*. 2004. vol. 279, No. 34, 359033-13.
Eilers, A. et al., "Direct inhibition of c-Jun N-terminal kinase in sympathetic neurons prevents c-jun-promoter activation and NGF withdrawal-induced death" *Journal of Neurochemistry*, 1998. 76, 1439-54.
Eilers, A. et al., "Role of the Jun Kinase Pathway in the Regulation of c-Jun Expression and Apoptosis in Sympathetic Neurons" *The Journal of Neuroscience*. 1998 . 8(5), 1713-24.
Estus, S. et al., "Aggregated Amyloid-β Protein Induces Cortical Neuronal Apoptosis and Concomitant "Apoptotic" Pattern of Gene Induction." *The Journal of Neuroscience*. 1997. 17(20), 7736-45.
Ham, J. et al., "A c-Jun Dominant Negative Mutant Protects Sympathetic Neurons against Programmed Cell Death" *Neuron*. 1995. vol. 14, 927-39.
Lisnock, J. et al., "Activation of JNK3α1 Requires both MKK4 and MKK7: Kinetic Characterization of in Vitro Phosphorylated JNK3α1" *Biochemistry*. 2000. vol. 39, 3141-48.
Watson, A. et al., "Phosphorylation of c-Jun Is Necessary for Apoptosis Induced by Survival Signal Withdrawal in Cerebellar Granule Neurons" *The Journal of Neuroscience*. 1998. 18(2), 751-62.
Young, P. R. et al., "Pyridinyl Imidazole Inhibitors of p38 Mitogen-activated Protein Kinase Bind in the ATP Site" *The Journal of Biological Chemistry*, 1997. vol. 272, No. 18, 12116-21.

*Primary Examiner*—Bernard Dentz
(74) *Attorney, Agent, or Firm*—Wilmer Cutler Pickering Hale and Dorr LLP

(57) ABSTRACT

The present invention relates to novel 5-substituted 7-aza-indole compounds of formula (I), their use in the inhibition of c-Jun N-terminal kinases, their use in medicine and particularly in the prevention and/or treatment of neurodegenerative disorders related to apoptosis and/or inflammation. The invention also provides processes for manufacture of said compounds, compositions containing them and processes for manufacturing such compositions

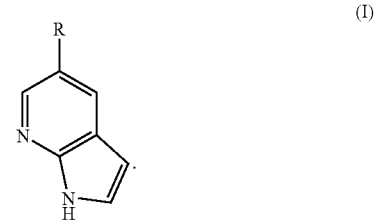

(I)

14 Claims, No Drawings

FOREIGN PATENT DOCUMENTS

| | | |
|---|---|---|
| EP | 1106621 A2 | 6/2001 |
| WO | WO-9921859 A1 | 5/1999 |
| WO | WO-0035909 A1 | 6/2000 |
| WO | WO-0035921 A1 | 6/2000 |
| WO | WO-0056710 A1 | 9/2000 |
| WO | WO-0112609 A1 | 2/2001 |
| WO | WO-0147922 A2 | 7/2001 |
| WO | WO-0149288 A1 | 7/2001 |
| WO | WO01049288 A1 * | 7/2001 |
| WO | WO-0216359 A1 | 2/2002 |
| WO | WO-02081475 A1 | 10/2002 |
| WO | WO-03082869 A1 | 10/2003 |

* cited by examiner

AZAINDOLES AS INHIBITORS OF C-JUN N-TERMINAL KINASES

The present invention relates to novel 5-substituted 7-azaindole compounds, their use in the inhibition of c-Jun N-terminal kinases, their use in medicine and particularly in the prevention and/or treatment of neurodegenerative disorders related to apoptosis and/or inflammation. The invention also provides processes for manufacture of said compounds, compositions containing them and processes for manufacturing such compositions.

c-Jun N-terminal kinases (hereinafter referred to as "JNKs") are members of the mitogen-activated protein kinase (MAPK) family. JNKs are involved in response to various stimuli, including proinflammatory cytokines and environmental stress. JNKs, and JNK3 in particular, play an important role during apoptotic death of cells and therefore have been implicated in various disorders including stroke, traumatic brain injury and other neurodegenerative diseases such as Parkinson disease, Alzheimer disease and others. Since JNK activity is a physiological regulator of AP-1 transcriptional activity, JNK inhibitors are expected to reduce inflammatory response.

Apoptosis is a form of cell death in which the cell actively participates in its own destruction in a process involving a characteristic series of biochemical and morphological changes which are regulated by specific cell death genes. The apoptotic cell death is a process that has been observed in the developing mammalian nervous system. In mice, the inactivation by homologous recombination of genes that encode proteins that promote apoptosis, such as the caspase-3 or the Bax protein, prevents developmental neuronal cell death. The destruction of genes that encode cell death suppressors such as Bcl-x, leads to enhanced neuronal cell death. There is increasing evidence that apoptosis plays an important role in the pathology of acute and chronic neurodegenerative diseases. For example, in transgenic mice overexpressing the anti-apoptotic Bcl-2 protein in the nervous system there is a decrease in infarct volume following cerebral ischemia. Similarly, injection of the caspase inhibitor BAF reduces neuronal cell death following hypoxia/ischaemia in neonatal rats. Another example is spinal muscular atrophy (a motor neurondisease) where loss of function mutations in the SMN gene is associated with the disease. Recent data has shown that the wild type SMN protein binds to Bcl-2 and co-operates with it to inhibit apoptosis. These results suggest that inhibitors of neuronal apoptosis could be beneficial in the treatment of human neurodegenerative diseases. There is increasing evidence that neuronal apoptosis is an important pathological feature of stroke, traumatic brain injury and other neurodegenerative diseases. Therefore, pharmacotherapy using inhibitors of neuronal apoptosis may provide a therapeutic benefit in neurodegenerative conditions.

A number of groups have studied the mechanisms of neuronal cell death using in vitro cell culture systems and the results suggest that in some systems the transcription factor c-Jun is activated by the removal of survival signals and promotes cell death.

Antibodies specific for c-Jun protected NGF-deprived rat sympathetic neurones from apoptosis. Analogous neuroprotection due to expression of a c-Jun dominant negative mutant has been demonstrated, whereas overexpression of wild type c-Jun protein was sufficient to induce apoptosis in the presence of NGF. Estus and co-workers recently showed that an increase in c-Jun RNA levels occurs in cortical neurones undergoing apoptosis after treatment with β-amyloid peptide (Estus et al., 1997, J. Neurosci. 17, 7736-7745). It has also been shown that c-Jun is required for apoptosis in cerebellar granule neurones deprived of survival signals.

c-Jun is activated by JNKs, which phosphorylate its transcriptional activation domain. In humans there are three JNK genes: JNK1, JNK2 and JNK3. The RNAs encoding JNK1 and JNK2 are expressed in many tissues, including the brain, but JNK3 is restricted to the nervous system and to a smaller extent the heart and testes.

JNKs are strongly activated in cellular responses to various stresses such as UV radiation, heat shock, osmotic shock, DNA-damaging agents, and proinflammatory cytokines such as TNFα, IL-1β and others. Upstream regulators of the JNK pathway include kinases such as SEK1, MKK7 and MEKK1. There is evidence that Jun kinase activity is required for neuronal apoptosis in vitro. Overexpression of MEKK1 in sympathetic neurones increased c-Jun protein levels and phosphorylation and induced apoptosis in the presence of NGF indicating that activation of the Jun kinase pathway can trigger neuronal cell death. The Jun kinase pathway has been shown to be necessary for the death of differentiated PC12 cells deprived of NGF. Furthermore, compound CEP-1347, which inhibits the c-Jun pathway (upstream of Jun kinase), protects motor neurones against cell death induced by survival factor withdrawal.

In JNK3 homozygous (−/−) knockout mice, epileptic seizures and death of hippocampal CA3 neurones induced by injection of kainic acid is blocked. This indicates that JNK3 is involved in certain forms of neuronal cell death in vivo. It is also a critical component of GluR6-mediated excitotoxicity. Furthermore, JNK3 (−/−) mice appear to develop normally and are viable suggesting that JNK3 is not essential for development or viability.

Strong nuclear JNK3 immunoreactivity in the brain CA1 neurones of patients with acute hypoxia suggests that JNK3 is involved in hypoxia-related neurodegeneration. Transient hypoxia, may also trigger apoptosis through JNK signaling pathway in developing brain neurones.

Furthermore, JNK3 immunoreactivity is colocalized with Alzheimer disease-affected neurones. Moreover JNK3 is related to neurofibrillary pathology of Alzheimer disease. In particular, JNK3 induces robust phosphorylation of amyloid precursor protein (APP) thus affecting its metabolism in disease state.

The present inventors have provided compounds which are inhibitors of c-Jun N-terminal kinases.

The first aspect of the present invention relates to a compound of formula (I) as defined below:

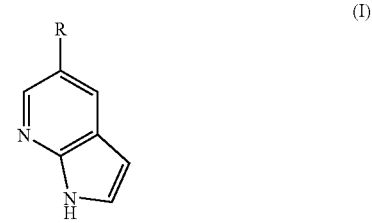

(I)

wherein:
R stands for carbocyclyl, substituted carbocyclyl, heterocyclyl, or substituted heterocyclyl, wherein
the optionally substituted carbocyclyl or optionally substituted heterocyclyl group is optionally fused to an unsaturated, partially unsaturated or fully saturated five to seven membered ring containing zero to three heteroatoms,
each substitutable carbon atom in R, including the optional fused ring, is optionally and independently substituted by one or more of $C_{1-12}$ alkyl, $C_{2-12}$ alkenyl, carbocyclyl, or heterocyclyl, halogen, haloalkyl, $OR^2$, $SR^2$, $NO_2$, CN, $NR^2R^2$, $NR^2COR^2$, $NR^2CONR^2R^2$, $NR^2COR^2$, $NR^2CO_2R^2$, $CO_2R^2$, $COR^2$, $CONR^2R^2$, $S(O)_2R^2$, $SONH_2$, $S(O)R^2$, $SO_2NR^2R^2$, $NR^2S(O)_2R^2$, wherein each $R^2$ may be the same or different and is as defined below and wherein:

the $C_{1-12}$ alkyl optionally incorporates one or two insertions selected from the group consisting of —O—, —C(O)—, —N($R^2$)—, —S(O)— and —S($O_2$)— wherein each $R^2$ may be the same or different and is as defined below;

the $C_{1-12}$ alkyl, carbocyclyl, or heterocyclyl group is optionally substituted by one or more of halogen, haloalkyl, $OR^2$, $SR^2$, $NO_2$, CN, $NR^2R^2$, $NR^2COR^2$, $NR^2CONR^2R^2$, $NR^2COR^2$, $NR^2CO_2R^2$, $CO_2R^2$, $COR^2$, $CONR^2_2$, $S(O)_2R^2$, $SONH_2$, $S(O)R^2$, $SO_2NR^2R^2$, $NR^2S(O)_2R^2$; wherein each $R^2$ may be the same or different and is as defined below and the carbocyclyl, or heterocyclyl group is optionally substituted by one or more $C_{1-12}$ alkyl, each saturated carbon in the optional fused ring is further optionally and independently substituted by =O, =S, =NNH$R^2$, NN$R^2R^2$, =N—O$R^2$, =NNHCO$R^2$, =NNHCO$_2R^2$, =NNSO$_2R^2$, or =N$R^2$, wherein each $R^2$ may be the same or different and is as defined below; and each substitutable nitrogen atom in R is optionally substituted by $R^3$, $COR^2$, $SO_2R^2$ or $CO_2R^2$, wherein each $R^2$ and $R^3$ may be the same or different and is as defined below;

$R^2$ is hydrogen, $C_{1-12}$ alkyl or aryl, optionally substituted by one or more of $C_{1-4}$ alkyl, halogen, $C_{1-4}$ haloalkyl, $OR^4$, $SR^4$, $NO_2$, CN, $NR^4R^4$, $NR^4COR^4$, $NR^4CONR^4R^4$, $NR^4COR^4$, $NR^4CO_2R^4$, $CO_2R^4$, $COR^4$, $CONR^4_2$, $S(O)_2R^4$, $SONH_2$, $S(O)R^4$, $SO_2NR^4R^4$, $NR^4S(O)_2R^4$, wherein the $C_{1-12}$ alkyl group optionally incorporates one or two insertions selected from the group consisting of —O—, —N($R^4$)—, —S(O)— and —S($O_2$)—, wherein each $R^4$ may be the same or different and is as defined below;

$R^3$ is $C_{1-12}$ alkyl or aryl, optionally substituted by one or more of $C_{1-4}$ alkyl, halogen, $C_{1-4}$ haloalkyl, $OR^4$, $SR^4$, $NO_2$, CN, $NR^4R^4$, $NR^4COR^4$, $NR^4CONR^4R^4$, $NR^4COR^4$, $NR^4CO_2R^4$, $CO_2R^4$, $COR^4$, $CONR^4_2$, $S(O)_2R^4$, $SONH_2$, $S(O)R^4$, $SO_2NR^4R^4$, $NR^4S(O)_2R^4$, wherein the $C_{1-12}$ alkyl group optionally incorporates one or two insertions selected from the group consisting of —O—, —N($R^4$)—, —S(O)— and —S($O_2$)—, wherein each $R^4$ may be the same or different and is as defined below;

$R^4$ is hydrogen, $C_{1-4}$ alkyl, or $C_{1-4}$ haloalkyl;

with the proviso that when R is phenyl substituted with branched $C_6$-alkyl (—CH(CH$_2$—CH(CH$_3$)CH$_3$))—CH$_2$—) incorporating two insertions —(CO)— and —NH—, the $C_6$-alkyl group is not substituted with CN;

and the pharmaceutically acceptable salts, and other pharmaceutically acceptable biohydrolyzable derivatives thereof, including esters, amides, carbamates, carbonates, ureides, solvates, hydrates, affinity reagents or prodrugs thereof.

For the avoidance of doubt, when a group as defined above contains two or more radicals, e.g. the radical $R^2$, as for example in the groups $SO_2NR^2R^2$ and $NR^2COR^2$, the radicals $R^2$ may be the same or different.

For the purposes of this invention, "alkyl" means a straight chain or branched alkyl radical of 1 to 12 carbon atoms, preferably 1 to 6 carbon atoms and most preferably 1 to 4 carbon atoms including but not limited to methyl, ethyl, n-propyl, isopropyl, n-butyl, sec-butyl, isobutyl, tert-butyl etc. The term "alkenyl" means a straight chain or branched alkylenyl radical of 2 to 12 carbon atoms, preferably 2 to 6 carbon atoms and most preferably 2 to 4 carbon atoms, and containing one or more carbon-carbon double bonds and includes but is not limited to ethylene, n-propyl-1-ene, n-propyl-2-ene, isopropylene, etc. The term "alkynyl" means a straight chain or branched alkynyl radical of 2 to 12 carbon atoms, preferably 2 to 6 carbon atoms and most preferably 2 to 4 carbon atoms, and containing one or more carbon-carbon triple bonds and includes but is not limited to ethynyl, 2-methylethynyl etc. The term "cycloalkyl" means an saturated or partly unsaturated 3-12 membered cyclic alkyl group and includes but not limited to cyclopropyl, cyclobutyl, cyclopentyl, cyclohexyl etc. Cycloalkyl groups may be optionally substituted or fused to one or more aryl, heterocyclyl or cycloalkyl group. "Heterocycloalkyl" means a 3-12 membered saturated or partly unsaturated cycloalkyl containing one or more hetero atom selected from N, S and O. "Haloalkyl" means an alkyl radical substituted with one or more halide atoms for example $CH_2CH_2Br$, $CF_3$ or $CCl_3$.

"Carbocyclyl" relates to a saturated, partly unsaturated or unsaturated 3-10 membered hydrocarbon ring, including cycloalkyl and aryl.

"Aryl" means an aromatic 3-10 membered hydrocarbon containing one ring or being fused to one or more saturated or unsaturated rings including but not limited to phenyl, napthyl, anthracenyl or phenanthracenyl.

"Heteroaryl" means an aromatic 3-10 membered aryl containing one or more heteroatoms selected from N, O or S and containing one ring or being fused to one or more saturated or unsaturated rings and.

"Heterocyclyl" means a 3-10 membered ring system containing one or more heteroatoms selected from N, O or S and includes heteroaryl. The heterocyclyl system can contain one ring or may be fused to one or more saturated or unsaturated rings; the heterocyclyl can be fully saturated, partially saturated or unsaturated and includes but is not limited heteroaryl and heterocarbocyclyl, e.g. cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, and trithiane.

Halogen means F, Cl, Br or I, preferably F.

R is preferably substituted with one or more of alkyl (e.g. methyl, ethyl or propyl), haloalkyl (preferably $CF_3$), halogen (e.g. F, Cl or Br, preferably F), $OR^8$, $SR^8$, $SOR^8$, $(NR^8)_2$, wherein $R^8$ is independently selected from hydrogen, $C_{1-4}$ alkyl or haloalkyl and is preferably phenyl or napthyl. When R is phenyl it is preferably substituted in the 4-(para) position, e.g. by $NR^6R^6$, where $R^6$ stands independently for H or $C_{1-4}$ alkyl.

Representative compounds according to the first aspect of the invention are illustrated below.

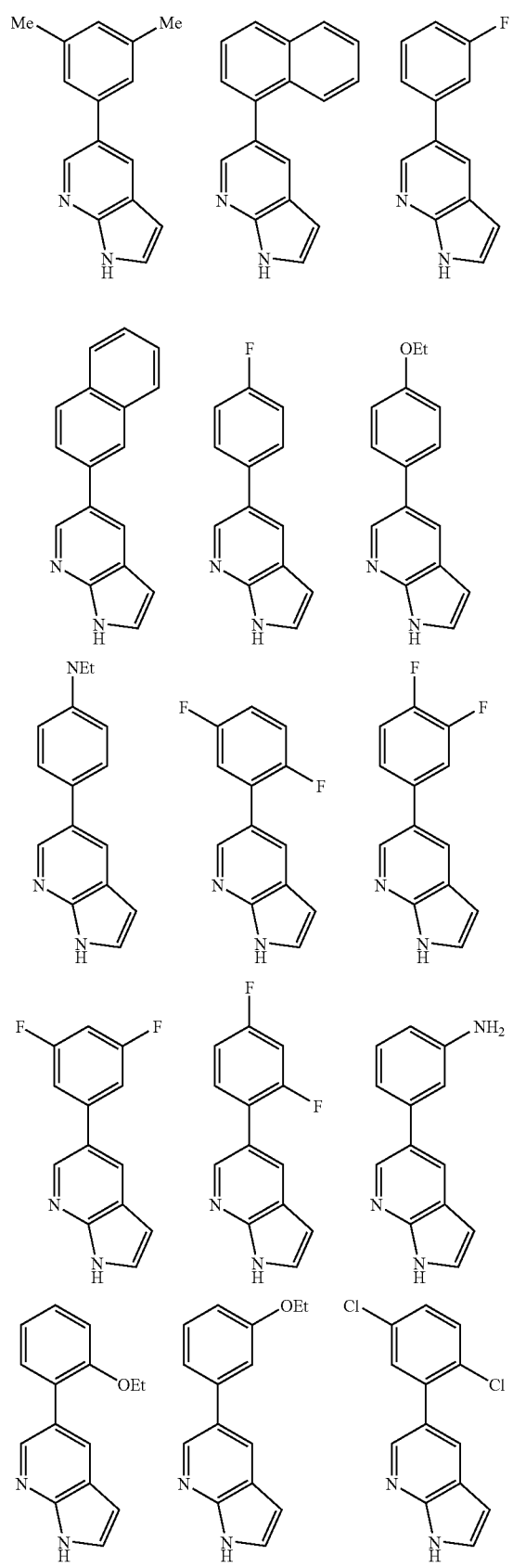
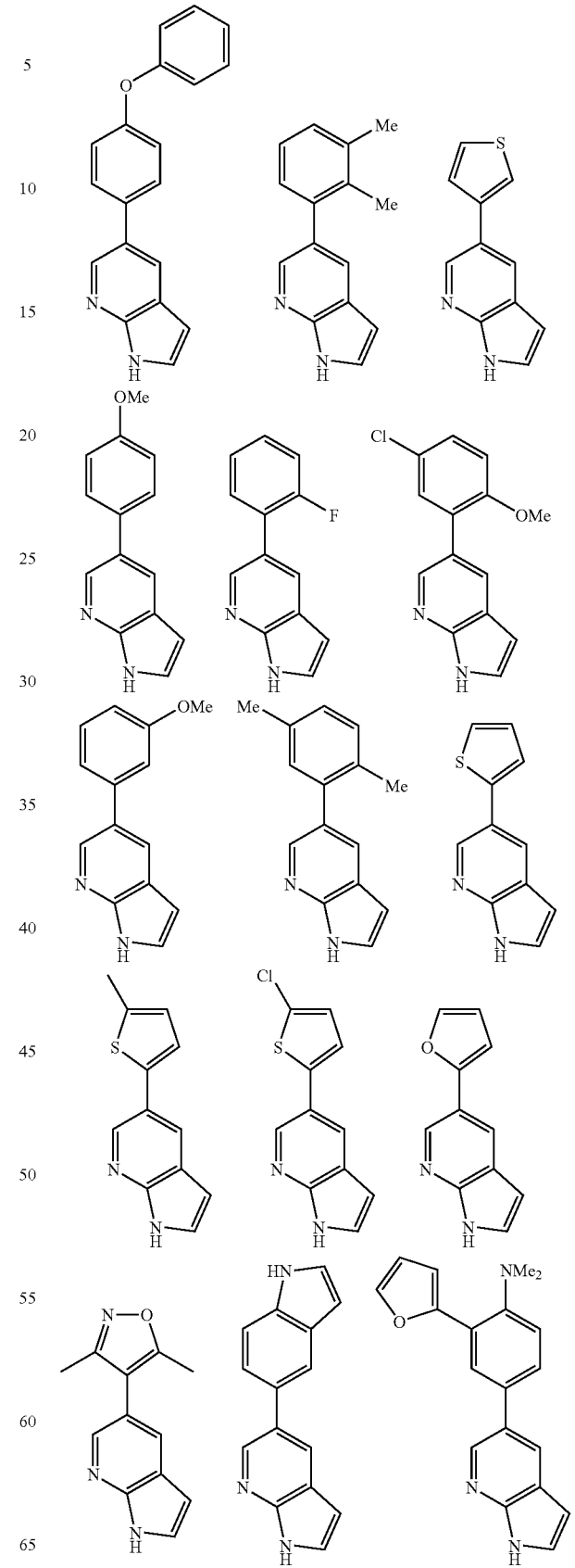

-continued
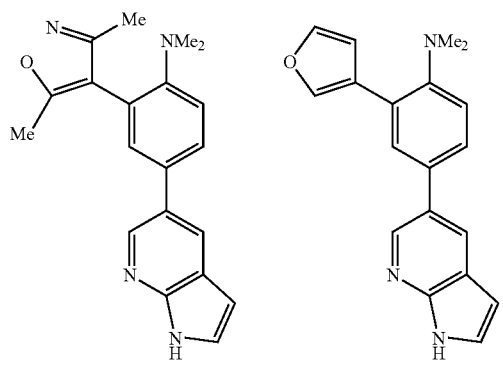
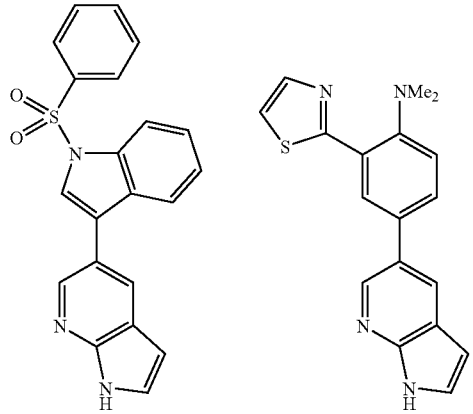
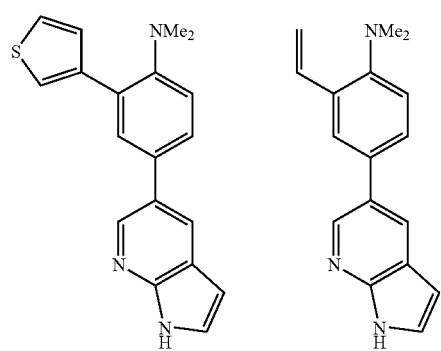
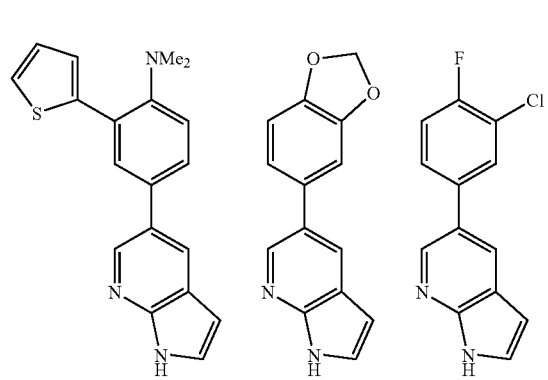
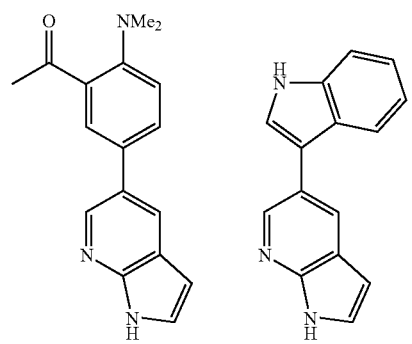
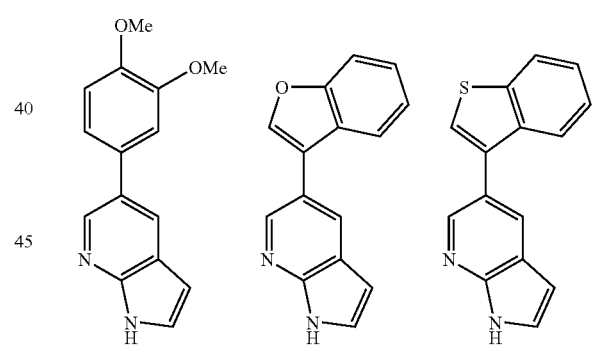
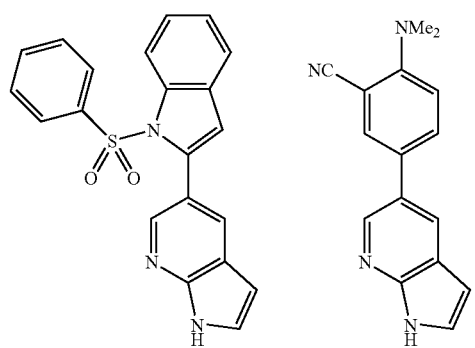
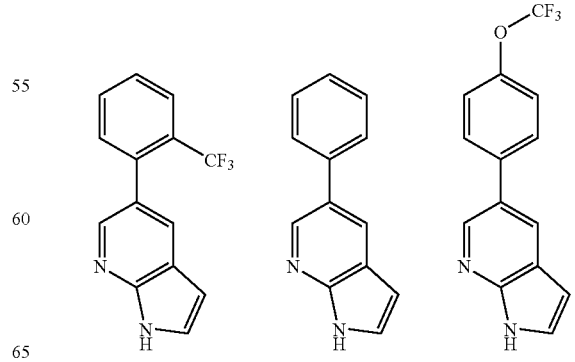

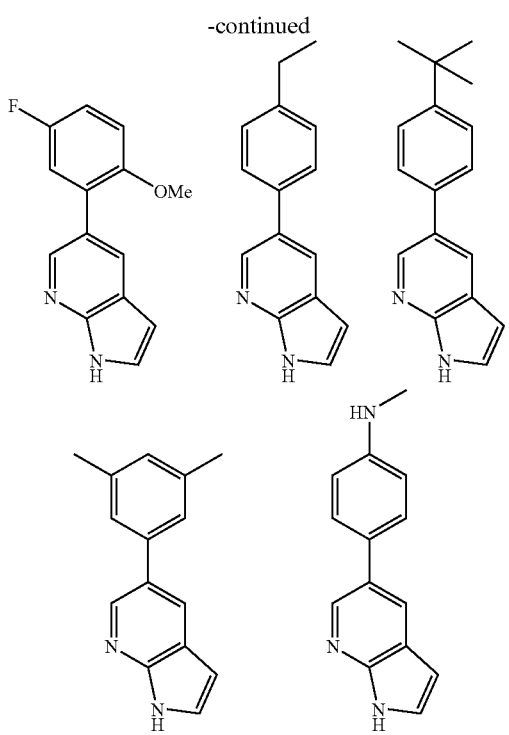

The compounds of the invention may be provided as a salt, preferably as a pharmaceutically acceptable salt of compounds of formula (I). Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl)aminomethane; and the like.

Salts may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

The invention also extends to a prodrug of the aforementioned compounds. A prodrug is any compound that may be converted under physiological conditions or by solvolysis to any of the compounds of the invention or to a pharmaceutically acceptable salt of the compounds of the invention. A prodrug may be inactive when administered to a subject but is converted in vivo to an active compound of the invention.

The compounds of the invention may contain one or more asymmetric carbon atoms and may exist in racemic and optically active forms. The first aspect of the invention covers all of these compounds.

In accordance with the second aspect of the present invention, the compound of the general formula (I):

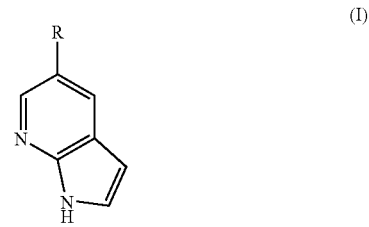

can be made by hydrogenating a compound of the general formula (II):

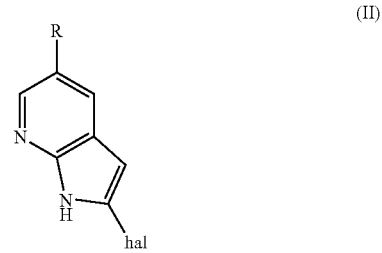

in which R is as defined above and hal stands for a halogen atom, principally F or Cl, e.g. using in the presence of a suitable metal catalyst, such as e.g. palladium on activated carbon, and suitable amine such as e.g. triethylamine. The reaction can be run using a solution of compound (II) in a single solvent (e.g. alcohol, such as methanol or ethanol) or a mixture of solvents including e.g. an alcohol, dichloromethane, chloroform, etc.

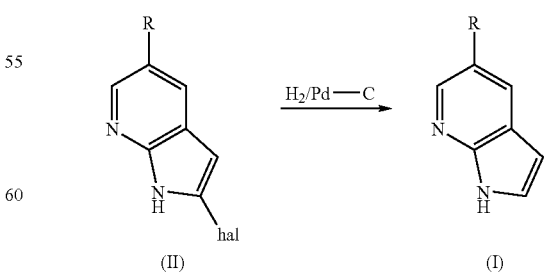

The compound of the general formula (II) can be made by halogenating a compound of the general formula (III) in the 2 position, e.g.:

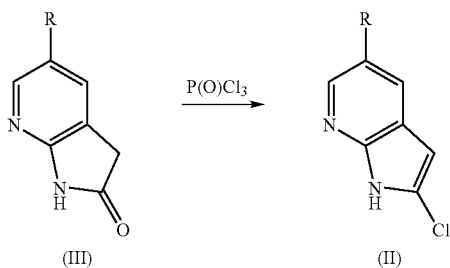

where R is as defined above, e.g. using P(O)Cl$_3$ at elevated temperature (about 100° C.).

The compound of the general formula (III) can be made from 7-azaindole according to processes known in the art, see for example Glennon, K. C. et al. (WO00/56710) and Viaud, M.-C. et al. (EP0737685) and Cheung, M. et al. (WO99/21859). An example of a suitable scheme for the production of the compound of the general formula (III) is:

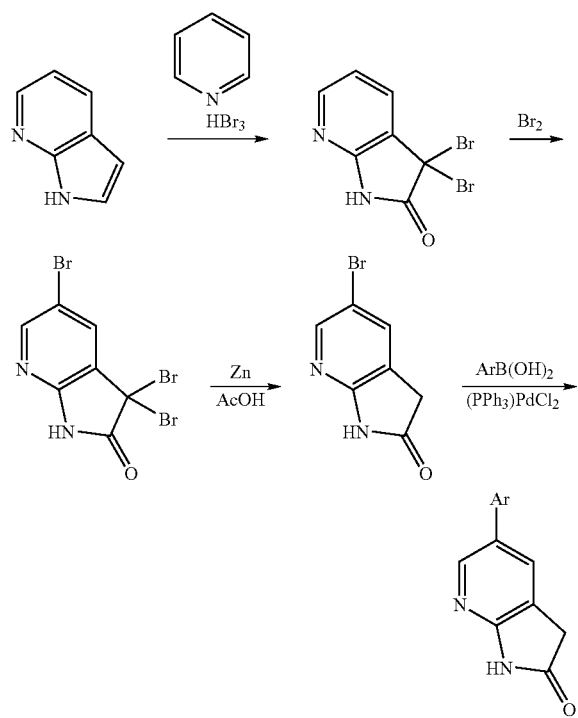

The third aspect of the present invention provides a composition comprising a compound of the general formula (I) as defined above in combination with a pharmaceutically acceptable carrier, diluent or excipient.

The composition may also comprise one or more additional active agent, such as an anti-inflammatory agent (for example a p38 inhibitor, glutamate receptor antagonist, or a calcium channel antagonist), a chemotherapeutic agent and/or an antiproliferative agent.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

In addition, the present invention provides a process for the manufacture of a composition according to the invention, as described above. The manufacture can be carried out by standard techniques well known in the art and involves combining a compound according to the first aspect of the invention and the pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

The present invention provides a compound of the first aspect or a composition of the third aspect for use in therapy/medicine.

The fourth aspect of the present invention relates to a compound of the general formula I as defined below

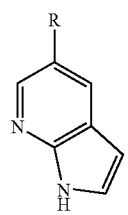

(I)

or a composition containing the compound, for use in inhibiting JNK wherein:

R stands for carbocyclyl, substituted carbocyclyl, heterocyclyl, or substituted heterocyclyl, wherein the optionally substituted carbocyclyl or optionally substituted heterocyclyl group is optionally fused to an unsaturated, partially unsaturated or fully saturated five to seven membered ring containing zero to three heteroatoms, each substitutable carbon atom in R, including the optional fused ring, is optionally and independently substituted by one or more of $C_{1-12}$ alkyl, $C_{2-12}$ alkenyl, carbocyclyl, or heterocyclyl, halogen, haloalkyl, $OR^2$, $SR^2$, $NO_2$, CN, $NR^2R^2$, $NR^2COR^2$, $NR^2CONR^2R^2$, $NR^2COR^2$, $NR^2CO_2R^2$, $CO_2R^2$, $COR^2$, $CONR^2{}_2$, $S(O)_2R^2$, $SONH_2$, $S(O)R^2$, $SO_2NR^2R^2$, $NR^2S(O)_2R^2$, wherein each $R^2$ may be the same or different and is as defined below and wherein:

the $C_{1-12}$ alkyl optionally incorporates one or two insertions selected from the group consisting of —O—, —C(O)—, —N($R^2$)—, —S(O)— and —S(O$_2$)— wherein each $R^2$ may be the same or different and is as defined below;

the $C_{1-12}$ alkyl, carbocyclyl, or heterocyclyl group is optionally substituted by one or more of halogen, haloalkyl, $OR^2$, $SR^2$, $NO_2$, CN, $NR^2R^2$, $NR^2COR^2$, $NR^2CONR^2R^2$, $NR^2COR^2$, $NR^2CO_2R^2$, $CO_2R^2$, $COR^2$, $CONR^2{}_2$, $S(O)_2R^2$, $SONH_2$, $S(O)R^2$, $SO_2NR^2R^2$, $NR^2S(O)_2R^2$; wherein each $R^2$ may be the same or different and is as defined below and the carbocyclyl, or heterocyclyl group is optionally substituted by one or more $C_{1-12}$ alkyl, each saturated carbon in the optional fused ring is further optionally and independently substituted by =O, =S, =NNHR$^2$, NNR$^2$R$^2$, =N—OR$^2$, =NNHCOR$^2$, =NNHCO$_2$R$^2$, =NNSO$_2$R$^2$, or =NR$^2$, wherein each $R^2$ may be the same or different and is as defined below; and each substitutable nitrogen atom in R is optionally substituted by $R^3$, $COR^2$, $SO_2R^2$ or $CO_2R^2$, wherein each $R^2$ and $R^3$ may be the same or different and is as defined below;

$R^2$ is hydrogen, $C_{1-12}$ alkyl or aryl, optionally substituted by one or more of $C_{1-4}$ alkyl, halogen, $C_{1-4}$ haloalkyl, $OR^4$, $SR^4$, $NO_2$, CN, $NR^4R^4$, $NR^4COR^4$, $NR^4CONR^4R^4$, $NR^4COR^4$, $NR^4CO_2R^4$, $CO_2R^4$, $COR^4$, $CONR^4{}_2$, $S(O)_2R^4$, $SONH_2$, $S(O)R^4$, $SO_2NR^4R^4$, $NR^4S(O)_2R^4$, wherein the $C_{1-2}$ alkyl group optionally incorporates one or two insertions selected from the group consisting of —O—, —N($R^4$)—, —S(O)— and —S(O$_2$)—, wherein each $R^4$ may be the same or different and is as defined below;

$R^3$ is $C_{1-12}$ alkyl or aryl, optionally substituted by one or more of $C_{1-4}$ alkyl, halogen, $C_{1-4}$ haloalkyl, $OR^4$, $SR^4$, $NO_2$, CN, $NR^4R^4$, $NR^4COR^4$, $NR^4CONR^4R^4$, $NR^4COR^4$, $NR^4CO_2R^4$, $CO_2R^4$, $COR^4$, $CONR^4{}_2$, $S(O)_2 R^4$, $SONH_2$, $S(O)R^4$, $SO_2 NR^4R^4$, $NR^4S(O)_2R^4$, wherein the $C_{1-12}$ alkyl group optionally incorporates one or two insertions selected from the group consisting of —O—, —N($R^4$)—, —S(O)— and —S(O$_2$)—, wherein each $R^4$ may be the same or different and is as defined below;

$R^4$ is hydrogen, $C_{1-4}$ alkyl, or $C_{1-4}$ haloalkyl;

and the pharmaceutically acceptable salts, and other pharmaceutically acceptable biohydrolyzable derivatives thereof, including esters, amides, carbamates, carbonates, ureides, solvates, hydrates, affinity reagents or prodrugs thereof.

All preferred options for R, $R^2$, $R^3$ and $R^4$ and any substitutions or insertions thereof are as set out in the first aspect of the present invention. Preferred features of the composition of the fourth aspect are set out in the third aspect.

The compounds of the fourth aspect of the present invention are inhibitors of JNK, such as JNK1, JNK2, or JNK3. In particular, the compounds of the present invention are inhibitors of JNK3. Preferably, the compounds of the present invention inhibit JNK3 specifically.

One advantage of the compounds of the present invention is that they show a good stability to liver microsomes, at least when tested in vitro and hence are are not rapidly metabolically removed from the body.

The compounds are therefore useful for conditions for which inhibition of JNK activity is beneficial. Thus, preferably, this aspect provides a compound of the general formula (I), or a composition containing a compound of formula (I) as defined in the fourth aspect of the present invention, as described above, for the prevention or treatment of a JNK-mediated disorder. The compounds of the general formula I may thus be used for the inhibition of JNK, more preferably for the inhibition of JNK3.

A "JNK-mediated disorder" is any disease or deleterious condition in which JNK plays a role. Examples include neurodegenerative disorder (including dementia), inflammatory disease, a disorder linked to apoptosis, particularly neuronal apoptosis, autoimmune disease, destructive bone disorder, proliferative disorder, cancer, infectious disease, allergy, ischemia reperfusion injury, heart attack, angiogenic disorder, organ hypoxia, vascular hyperplasia, cardiac hypertrophy, thrombin induced platelet aggregation and any condition associated with prostaglandin endoperoxidase synthase-2. The compounds of the present invention may be used for any of these JNK-mediated disorders.

The compounds of the fourth aspect of the present invention are particularly useful for the prevention or treatment of a neurodegenerative disorder. In particular, the neurodegenerative disorder results from apoptosis and/or inflammation. Examples of neurodegenerative disorders are: dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia; dementia linked to meningitis and/or neurosis; cerebrovascular dementia; or dementia in an HIV-infected patient.

The neurodegenerative disorder may be a peripheral neuropathy, including mononeuropathy, multiple mononeuropathy or polyneuropathy. Examples of peripheral neuropathy may be found in diabetes mellitus, Lyme disease or uremia; peripheral neuropathy caused by a toxic agent; demyelinating disease such as acute or chronic inflammatory polyneuropathy, leukodystrophies, or Guillain-Barré syndrome; multiple mononeuropathy secondary to a collagen vascular disorder (e.g. polyarteritis nodosa, SLE, Sjögren's syndrome); multiple mononeuropathy secondary to sarcoidosis; multiple mononeuropathy secondary to a metabolic disease (e.g. diabetes or amyloidosis); or multiple mononeuropathy secondary to an infectious disease (e.g. Lyme disease or HIV infection).

The compounds of the invention can also be used to prevent or treat disorders resulting from inflammation. These include, for example, inflammatory bowel disorder, bronchitis, asthma, acute pancreatitis, chronic pancreatitis, allergies of various types, and possibly Alzheimer's disease. Autoimmune diseases which may also be treated or prevented by the compounds of the present invention include rheumatoid arthritis, systemic lupus erythematosus, glumerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myastlhenia gravis, multiple sclerosis, ulcerative colitis, Crohn's disease, psoriasis or graft vs host disease.

A compound of the present invention may be administered simultaneously, subsequently or sequentially with one or more other active agent, such as an anti-inflammatory agent e.g. p38 inhibitor, glutamate receptor antagonist, calcium channel antagonist, a chemotherapeutic agent or an antiproliferative agent. For example, for acute treatment, a p38 inhibitor may be administered to a patient prior to administering a compound of the present invention.

The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Accordingly the fifth aspect of the present invention relates to a method of treating or preventing a JNK-mediated disorder in an individual, which method comprises administering to said individual a compound as defined in the fourth aspect or a composition containing that compound. The active compound is preferably administered in a cumulative effective amount. The individual may be in need of the treatment or prevention. Any of the JNK-mediated disorders listed above in relation to the fourth aspect may be the subject of treatment or prevention according to the fifth aspect. One or more other active agent may be administered to the individual simultaneously, subsequently or sequentially to administering the compound. The other active agent may be an anti-inflammatory agent such as a p38 inhibitor, glutamate receptor antagonist, calcium channel antagonist, a chemotherapeutic agent or an antiproliferative agent, but is preferably p38 inhibitor for acute treatment.

The sixth aspect of the present invention provides the use of a compound of the general formula (I) as defined in the fourth aspect of the invention in the manufacture of a medicament for the prevention or treatment of a JNK-mediated disorder. The medicament may be used for treatment or prevention of any of the JNK-mediated disorders listed above in relation to the fourth aspect. Again, the compound of the present invention may be administered simultaneously, subsequently or sequentially with one or more other active agent, preferably a p38 inhibitor for acute treatment.

According to the seventh aspect of the present invention, there is also provided an assay for determining the activity of the compounds of the present invention, comprising providing a system for assaying the activity and assaying the activity of the compound. Preferably the assay is for the INK inhibiting activity of the compound, more preferably it is for the JNK3-specific inhibiting activity of the compounds. The compounds of the invention may be assayed in vitro, in vivo, in silico, or in a primary cell culture or a cell line. In vitro assays include assays that determine inhibition of either the kinase activity or ATPase activity of activated JNK. Alternatively, in vitro assays may quantitate the ability of a compound to bind JNK and may be measured either by radiolabelling the compound prior to binding, then isolating the inhibitor/JNK complex and determining the amount of the radiolabel bound or by running a competition experiment where new inhibitors are incubated with JNK bound to known radioligands. An example of an assay which may be used is Scintillation Proximity Assay (SPA), preferably using radiolabelled ATP. Another example is ELISA. Any type or isoform of JNK may be used in these assays.

In a yet further aspect of the present invention, there is provided a method of inhibiting the activity or function of a JNK, particularly JNK3, which method comprises exposing a JNK to a compound or a composition of the first or fourth aspect of the present invention. The method may be performed in a research model, in vitro, in silico, or in vivo such as in an animal model. A suitable animal model may be a kainic acid model in rat or mice, traumatic brain injury model in rat, or MPTP in mice.

All features of each of the aspects apply to all other aspects mutatis mutandis.

Below, the present invention is illustrated using non-limiting examples.

EXAMPLES

Synthesis of Example 5-substituted 7-azaindole Derivative 7

Scheme 1

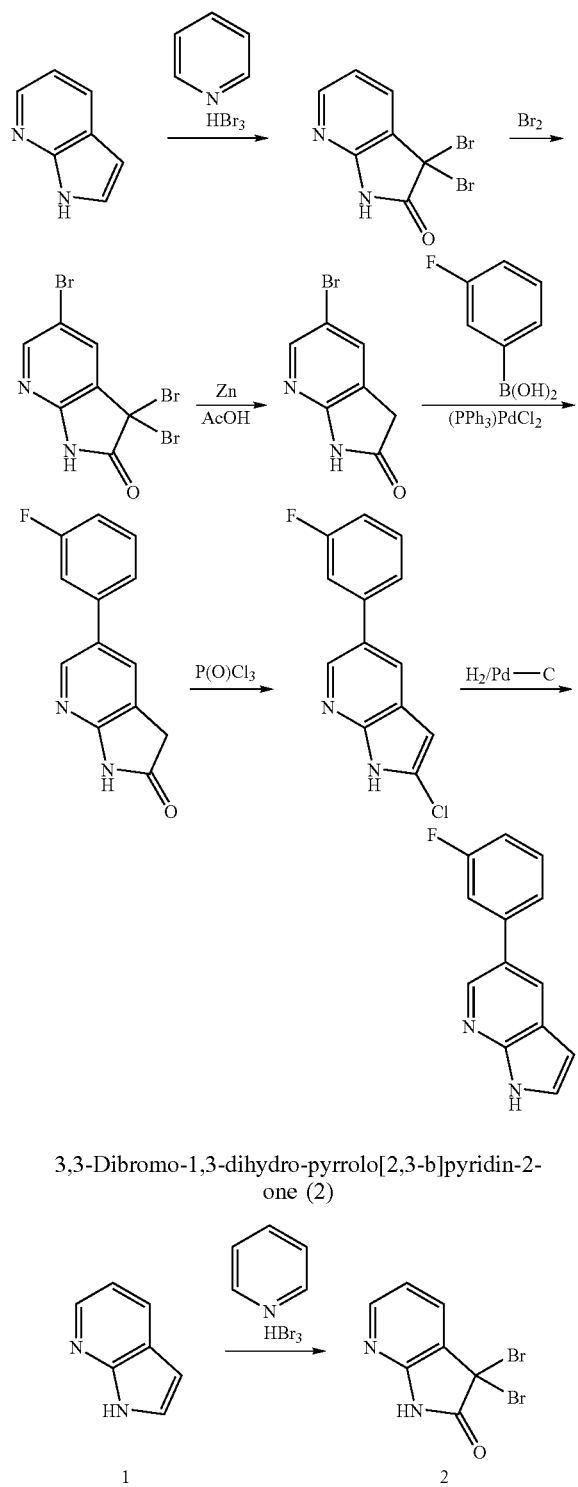

3,3-Dibromo-1,3-dihydro-pyrrolo[2,3-b]pyridin-2-one (2)

Technical (90%) pyridinium tribromide (220.4 g, 0.62 mol) was added portionwise over a period of 30 min to a stirred suspension of 7-azaindole (1, 27.13 g, 0.23 mol) in t-BuOH (1.36 L). The mixture was stirred at r.t for 3 h, and more pyridinium tribromide (73.3 g, 0.21 mol) was added in one portion. After additional stirring at r.t. for 2 h, the solvent was evaporated under reduced pressure. The residue was separated between water:AcOEt=1:1 (4.2 L). The aqueous layer was extracted with AcOEt (2×800 mL). Combined organic solutions were washed with water (2×500 mL), brine, dried (MgSO$_4$) and concentrated to dyness in vacuum. The residue was triturated with CH$_2$Cl$_2$ (1500 mL) for 20 min. The solid was filtered off, washed with CH$_2$Cl$_2$ (250 mL) and dried in vacuum to afford 2 (49.85 g, 75%) as yellow powder. $^1$H NMR (400 MHz, DMSO-d$_6$) δ 7.16 (dd, J=7.4, 5.1 Hz, 1H), 7.98 (dd, J=7.4, 1.5 Hz, 1H), 8.19 (dd, J=5.1, 1.5 Hz, 1H), 11.97 (bs, 1H).

3,3,5-Tribromo-1,3-dihydro-pyrrolo[2,3-b]pyridin-2-one (3)

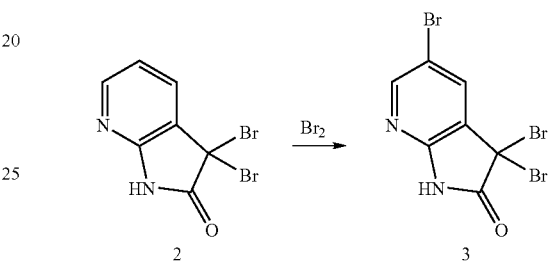

Bromine (13.4 mL, 0.262 mol) was added dropwise over a period of 30 min to a cooled (ice bath) and stirred suspension of 2 (37.86 g, 0.131 mol) in water:t-BuOH=1:1 (1500 mL). Cooling bath was removed and the mixture was stirred at r.t. overnight. Then the solution was cooled to 15° C. and saturated aqueous solution of NaHCO$_3$ (278 mL) was added. A yellow suspension, which was formed, was concentrated in vacuum (bath temperature<32° C.) until about 1000 mL of condensate was collected. The solid was filtered off, washed with water (200 mL), and dried in vacuum to afford 3 (40.85 g, 85%) as tan powder.

5-Bromo-1,3-dihydro-pyrrolo[2,3-b]pyridin-2-one (4)

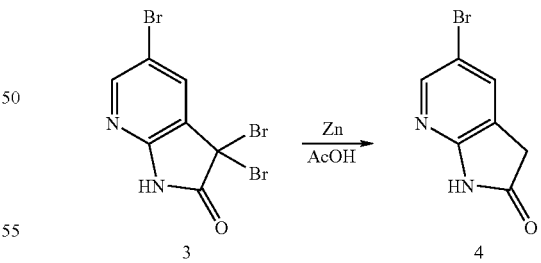

Zinc dust (34.0 g, 0.52 mol) was added in small portion to a stirred suspension of 3 (40.85 g, 0.111 mol) in glacial acetic acid (1000 mL) at such a rate that the temperature was maintained between 20-25° C. (strongly exothermic reaction; external ice bath cooling). Addition took about 20 min. Cooling bath was removed and stirring was continued at r.t. for 2 h. The solid was filtered off, washed with toluene (50 mL) and triturated with CH$_2$Cl$_2$:MeOH=4:1 (2.5 L). The solution was decanted off and treated with 1.0 M aqueous Na$_2$CO$_3$ solution (170 mL). After stirring for 1 h the two layers were separated. The organic layer was washed again with 1.0 M aqueous Na$_2$CO$_3$ solution (50 mL). The combined aqueous layers were extracted with CH$_2$Cl$_2$:MeOH=4:1 (10×100 mL). Combined organic solutions were dried with MgSO$_4$ (200 g) and concentrated. The residual solid was dissolved in THF (2000 mL) and insoluble material was filtered off. The filtrate was concentrated to dryness in vacuum to afford 4 (16.93 g, 72%) as tan solid. $^1$H NMR (400 MHz, DMSO-d$_6$) δ 3.57 (s, 2H), 7.75 (m, 1H), 8.14 (m, 1H), 11.13 (bs, 1H).

5-(3-Fluoro-phenyl)-1,3-dihydro-pyrrolo[2,3-b]pyridin-2-one (5)

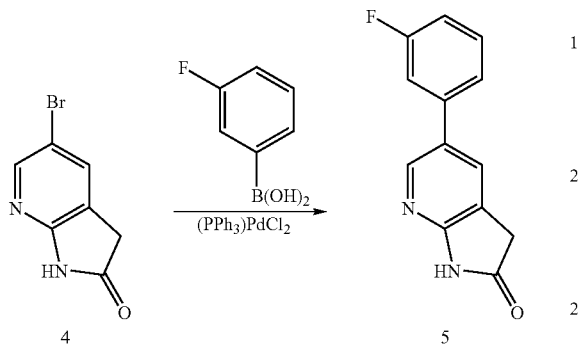

A mixture of 4 (16.63 g, 78.5 mmol), 3-fluorophenylboronic acid (16.47 g, 117.7 mmol), Pd(PPh$_3$)$_2$Cl$_2$ (2.73 g, 6.60 mmol), LiCl (9.95 g, 0.23 mol), 1.0 M aqueous Na$_2$CO$_3$ solution (196 mL, 0.196 mol) in EtOH (470 mL)—toluene (470 mL) was refluxed overnight. More Pd(PPh$_3$)$_2$Cl$_2$ (1.30 g, 3.14 mmol) was added and reflux was continued for 24 h. The mixture was cooled, and the organic layer was separated and washed with brine (100 mL). The washings were combined with the aqueous layer and extracted with AcOEt (4×400 mL). Combined extracts were washed with brine, added to the organic layer and dried with MgSO$_4$. The solution was concentrated to dryness in vacuum to give 26.98 g of brown semisolid, which was triturated with ether:hexane=1:1 (2×500 mL). The residue was dried in vacuum to afford 5 (16.85 g, 94%) as tan solid, which was used in the next step without further purification. $^1$H NMR (400 MHz, CDCl$_3$) δ 3.66 (s, 2H), 7.08 (dddd, J=8.4, 8.2, 2.4, 0.9 Hz, 1H), 7.22 (ddd, J=10.0, 2.4, 1.7 Hz, 1H), 7.30 (ddd, J=8.1, 1.7, 0.9 Hz, 1H), 7.43 (ddd, J=8.2, 8.1, 6.0 Hz, 1H), 7.69 (s, 1H), 8.36 (d, J=2.1 Hz, 1H), 8.98 (bs, 1H).

2-Chloro-5-(3-fluoro-phenyl)-1H-pyrrolo[2,3-b]pyridine (6)

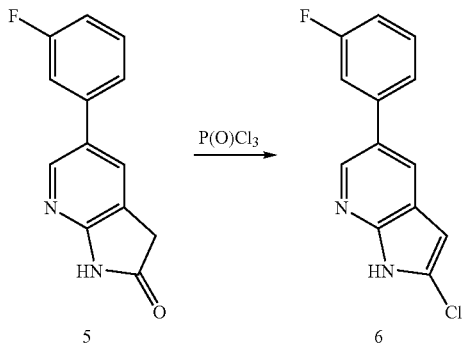

A suspension of 5 (16.52 g, 72.4 mmol) in neat P(O)Cl$_3$ (21.5 mL, 0.231 mol) was stirred at 100-105° C. for 4 h. The mixture was then cooled to r.t., diluted with p-xylene (100 mL) and concentrated to dryness in vacuum. The residue was separated between saturated aqueous NaHCO$_3$—AcOEt. 10% aqueous solution of Na$_2$CO$_3$ was added to basify the aqueous layer to pH 9. Organic phase was separated and the aqueous layer was extracted with AcOEt (8×300 mL). Combined organic solutions were dried MgSO$_4$, concentrated, and the residue was purified by silicagel chromatography (SGC) using CH$_2$Cl$_2$:AcOEt as eluent in gradient to afford recovered starting material 5 (0.76 g, 5%). The desired product was then crystallized from acetone to afford 6 (10.06 g, 56%), thin tan needles. $^1$H NMR (400 MHz, CDCl$_3$) δ 6.47 (s, 1H), 7.08 (tdd, J=8.1, 2.3, 1.5 Hz, 1H), 7.33 (ddd, J=9.9, 2.3, 1.6 Hz, 1H), 7.38-7.48 (m, 2H), 8.03 (d, J=2.1 Hz, 1H), 8.53 (d, J=2.1 Hz, 1H), 11.46 (bs, 1H).

5-(3-Fluoro-phenyl)-1H-pyrrolo[2,3-b]pyridine (7)

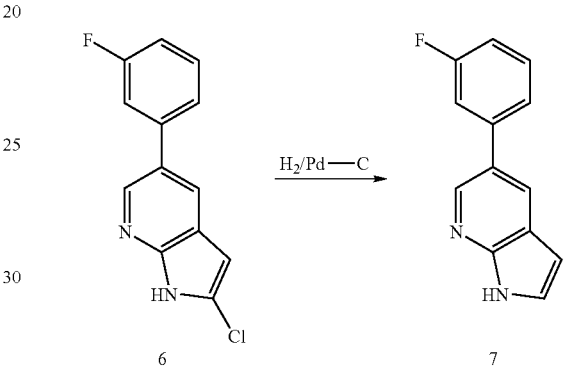

A mixture of chloride 6 (5.23 g, 21.3 mmol), 10% Pd/C (2.7 g), Et$_3$N (3.6 mL, 25.8 mmol) in THF:MeOH=5:1 (180 mL) was stirred under H$_2$ overnight. More 10% Pd/C (1.3 g) was added and stirring was continued for 3 h. Catalyst was removed by filtration and the solution was concentrated to dryness in vacuum. The residue was purified by SGC with CH$_2$Cl$_2$:AcOEt as eluent in gradient (up to 20% AcOEt) to afford 7 (5.23 g, 88%), greenish powder. $^1$H NMR (400 MHz, CDCl$_3$) δ 6.59 (dd, J=3.5, 2.0 Hz, 1H), 7.04-7.10 (m, 1H), 7.33-7.37 (m, 1H), 7.40-7.48 (m, 3H), 8.14 (d, J=2.1 Hz, 1H), 8.57 (d, J=2.1 Hz, 1H), 9.91 (bs, 1H).

JNK1, JNK2, JNK3—SPA Assay

A typical assay for testing the activity of compounds to inhibit JNK1, JNK2 and JNK3 enzymes is as follows:

1. Compound is dissolved in DMSO to a convenient concentration and this is diluted in 10% DMSO to a five times concentrate of the desired starting concentration (frequently 1:100).
2. 10 μl of 500 mM EDTA is added to alternative wells of the Opti-plate row, which will receive kinase reaction plus DMSO. This creates the negative control.
3. For the JNK2 and JNK3 assay, compounds are prepared in six 2-fold dilutions with water and each concentration is tested in duplicate. For the JNK1 assay compounds are prepared in four 5-fold dilutions with water which are tested in triplicate. Controls are treated identically.
4. 20 μl per well of each compound concentration is transferred to an Opti-plate, in duplicate.
5. 30 μl (JNK2/3 SPA) or 50 μl (JNK1 SPA) of substrate solution (25 mM HEPES pH 7.5, 10 mM magnesium acetate with 3.33 μM ATP (JNK2/3) or 2 μM ATP (JNK1), approximately 7.5 kBq [γ-33P] ATP, GST-c-Jun, in water) is added to each well.

6. 50 μl (JNK2/3 SPA) or 30 μl (JNK1 SPA) of kinase solution (JNK in 25 mM HEPES pH 7.5, 10 mM Mg Acetate) is added to each well.

| Kinase | Kinase per well (μg) | GST-c-Jun per well (μg) |
|---|---|---|
| JNK1 | 0.25 | 1 |
| JNK2 | 0.2 | 1.2 |
| JNK3 | 0.16 | 1.2 |

7. The plate is incubated for 30 minutes at room temperature.
8. 100 μl of bead/stop solution is added to each well (5 mg/ml glutathione-PVT-SPA beads, 40 mM ATP in PBS).
9. Plates are sealed and incubated for 30 minutes at room temperature, centrifuged for 10 minutes at 2500 g and counted.
10. The $IC_{50}$ values are calculated as the concentration of the compound being tested at which the phosphorylation of c-Jun is decreased to 50% of the control value. Example $IC_{50}$ values for the compounds of this invention are given in Table 1.

Examples of Inhibitory Potency Against JNK3 Kinase

TABLE 1

$IC_{50}$ values for selected compounds against JNK3 kinase

| Compound Number | Structure | JNK3 $IC_{50}$ (μM) |
|---|---|---|
| 1 | NMe₂ (structure) | 1.2 |
| 2 | (structure) | <0.5 |

The invention claimed is:

1. A compound of formula (I) as defined below:

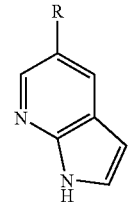

wherein:
R stands for carbocyclyl, substituted carbocyclyl, wherein
the optionally substituted carbocyclyl group is optionally fused to an unsaturated, partially unsaturated or fully saturated five to seven membered ring,
each substitutable carbon atom in R, including the optional fused ring, is optionally and independently substituted by one or more of $C_{1-12}$ alkyl, $C_{2-12}$ alkenyl, carbocyclyl, or heterocyclyl, halogen, haloalkyl, $OR^2$, $SR^2$, $NO_2$, CN, $NR^2R^2$, $NR^2COR^2$, $NR^2CONR^2R^2$, $NR^2COR^2$, $NR^2CO_2R^2$, $CO_2R^2$, $COR^2$, $CONR^2R^2$, $S(O)_2R^2$, $SONH_2$, $S(O)R^2$, $SO_2NR^2R^2$, $NR^2S(O)_2R^2$, wherein each $R^2$ may be the same or different and is as defined below and wherein:
the $C_{1-12}$ alkyl optionally incorporates one or two insertions selected from the group consisting of —O—, —C(O)—, —N($R^2$)—, —S(O)— and —S($O_2$)— wherein each $R^2$ may be the same or different and is as defined below;
the $C_{1-12}$ alkyl, carbocyclyl, or heterocyclyl group is optionally substituted by one or more of halogen, haloalkyl, $OR^2$, $SR^2$, $NO_2$, CN, $NR^2R^2$, $NR^2COR^2$, $NR^2CONR^2R^2$, $NR^2COR^2$, $NR^2CO_2R^2$, $CO_2R^2$, $COR^2$, $CONR^2_2$, $S(O)_2R^2$, $SONH_2$, $S(O)R^2$, $SO_2NR^2R^2$, $NR^2S(O)_2R^2$; wherein each $R^2$ may be the same or different and is as defined below and
the carbocyclyl, or heterocyclyl group is optionally substituted by one or more $C_{1-12}$ alkyl,
each saturated carbon in the optional fused ring is further optionally and independently substituted by =O, =S, =$NNHR^2$, $NNR^2R^2$, =N—$OR^2$, =$NNHCOR^2$, =$NNHCO_2R^2$, =$NNSO_2R^2$, or =$NR^2$, wherein each $R^2$ may be the same or different and is as defined below; and
each substitutable nitrogen atom in R is optionally substituted by $R^3$, $COR^2$, $SO_2R^2$ or $CO_2R^2$, wherein each $R^2$ and $R^3$ may be the same or different and is as defined below;
$R^2$ is hydrogen, $C_{1-12}$ alkyl or aryl, optionally substituted by one or more of $C_{1-4}$ alkyl, halogen, $C_{1-4}$ haloalkyl, $OR^4$, $SR^4$, $NO_2$, CN, $NR^4R^4$, $NR^4COR^4$, $NR^4CONR^4R^4$, $NR^4COR^4$, $NR^4CO_2R^4$, $CO_2R^4$, $COR^4$, $CONR^4_2$, $S(O)_2R^4$, $SONH_2$, $S(O)R^4$, $SO_2NR^4R^4$, $NR^4S(O)_2R^4$, wherein the $C_{1-12}$ alkyl group optionally incorporates one or two insertions selected from the group consisting of —O—, —N($R^4$)—, —S(O)— and —S($O_2$)—, wherein each $R^4$ may be the same or different and is as defined below;
$R^3$ is $C_{1-12}$ alkyl or aryl, optionally substituted by one or more of $C_{1-4}$ alkyl, halogen, $C_{1-4}$ haloalkyl, $OR^4$, $SR^4$, $NO_2$, CN, $NR^4R^4$, $NR^4COR^4$, $NR^4CONR^4R^4$, $NR^4COR^4$, $NR^4CO_2R^4$, $CO_2R^4$, $COR^4$, $CONR^4_2$, $S(O)_2R^4$, $SONH_2$, $S(O)R^4$, $SO_2NR^4R^4$, $NR^4S(O)_2R^4$, wherein the $C_{1-12}$ alkyl group optionally incorporates one or two insertions selected from the group consisting of —O—, —N(R⁴)—, —S(O)— and —S(O₂)—, wherein each R⁴ may be the same or different and is as defined below;

R⁴ is hydrogen, $C_{1-4}$ alkyl, or $C_{1-4}$ haloalkyl; with the proviso that when R is phenyl substituted with branched $C_6$-alkyl (—CH(CH₂—CH(CH₃)(CH₃))—CH₂—) incorporating two insertions —(CO)— and —NH—, the $C_6$-alkyl group is not substituted with —CN;

and the pharmaceutically acceptable salts thereof.

2. A compound as claimed in claim 1, wherein R is an aryl, optionally substituted with one or more of alkyl, haloalkyl, halogen, OR⁸, S R⁸, SO R⁸, (NR⁸)₂, wherein R⁸ is independently selected from hydrogen, $C_{1-4}$ alkyl or haloalkyl.

3. A compound as claimed in claim 1, wherein R is an optionally substituted aryl.

4. A compound as claimed in claim 3, wherein R is phenyl substituted in the 4-(para) position.

5. A compound as claimed in claim 4, wherein R is phenyl substituted by NR⁶R⁶; and wherein each R⁶ is independently H or $C_{1-4}$ alkyl.

6. A compound as claimed in claim 3, wherein R is aryl substituted with F, Cl, Br, haloalkyl, or alkyl.

7. A compound as claimed in claim 1, wherein the compound is selected from the group consisting of:

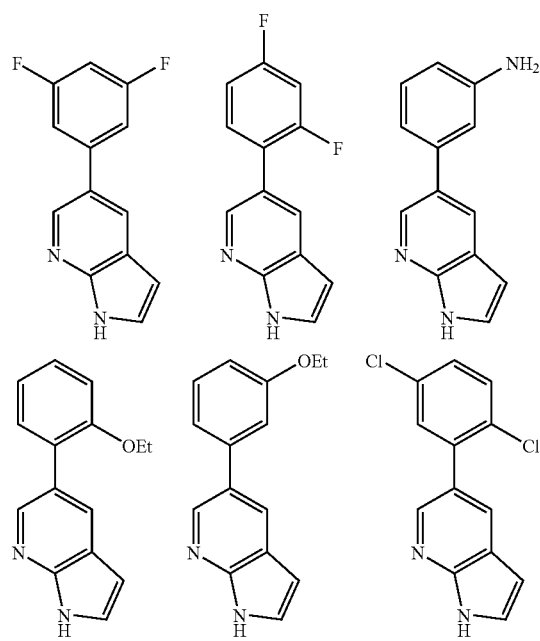

-continued

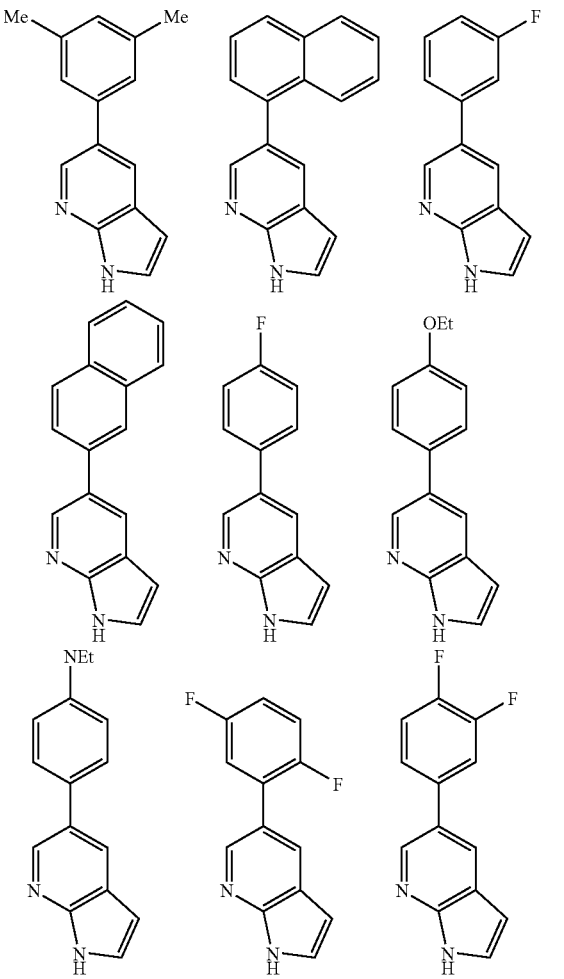

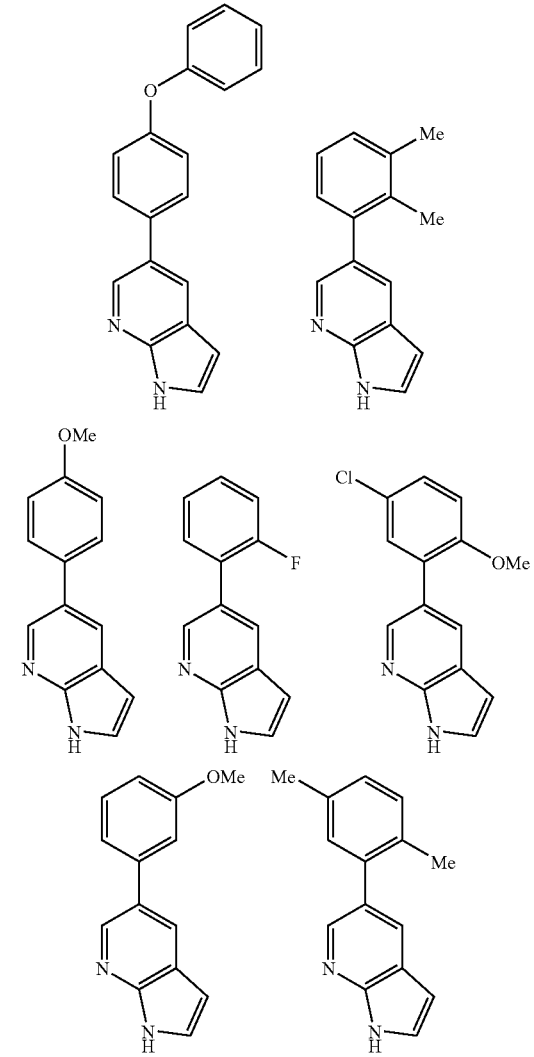

-continued
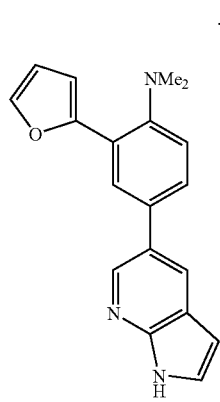 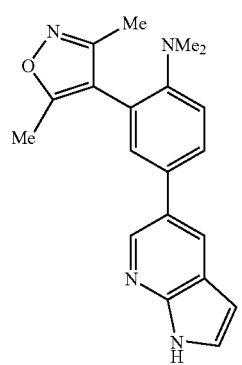 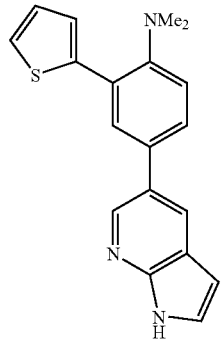 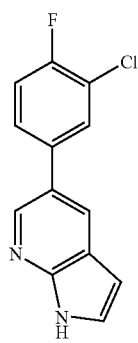
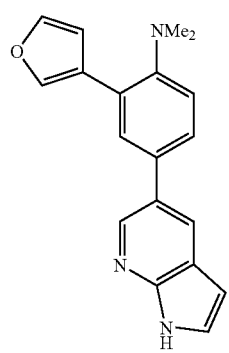 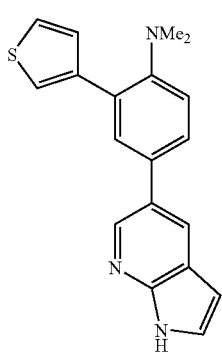 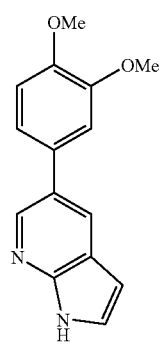 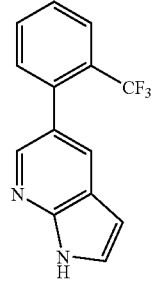
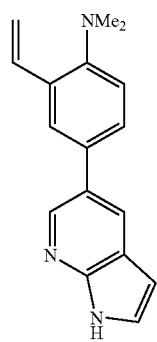 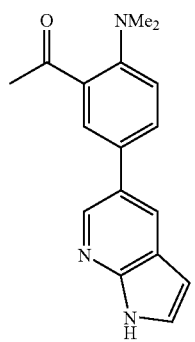 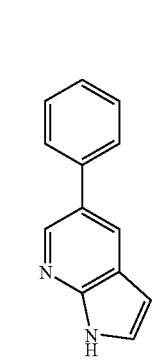 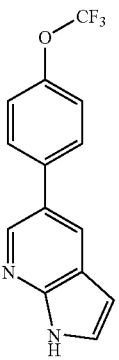
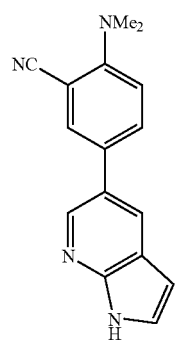 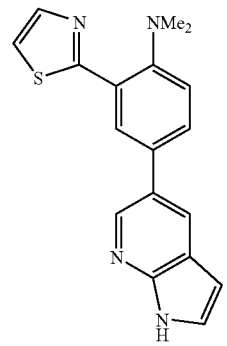 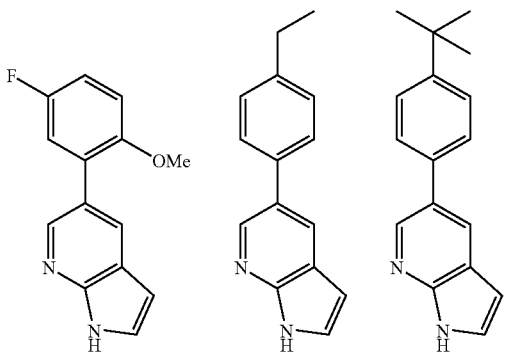

-continued

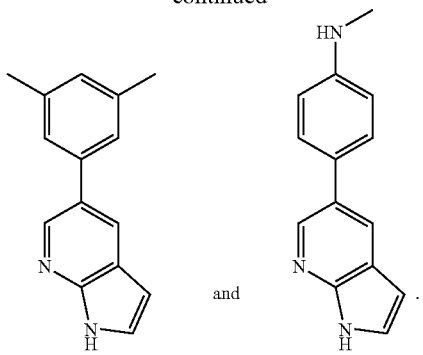

and

8. A process for the manufacture of the compounds of claim 1 which comprises hydrogenating a compound of the general formula (II):

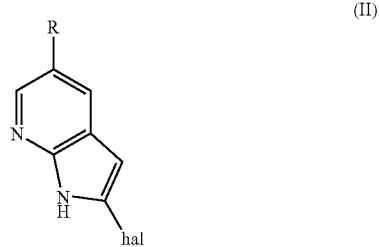

wherein R is as defined in claim 1 and hal stands for a halogen atom.

9. A process as claimed in claim 8, wherein the compound of the general formula (II) is made by halogenating a compound of the general formula (III) in the 2 position

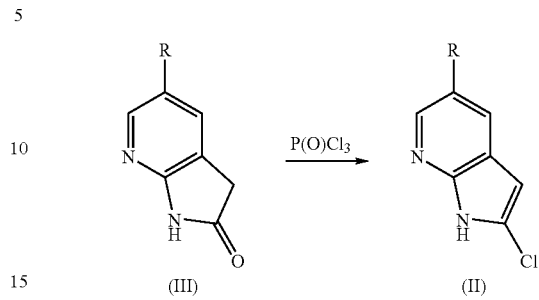

where R is as defined above and hal stands for halogen.

10. A pharmaceutical formulation comprising a compound as defined in claim 1 and a pharmaceutically acceptable carrier, diluent or excipient.

11. The compound of claim 3, wherein R is selected from the group consisting of phenyl and naphthyl.

12. The compound of claim 6, wherein R is aryl substituted with fluorine.

13. The compound of claim 6, wherein the haloalkyl is $CF_3$.

14. The compound of claim 6, wherein the alkyl is selected from the group consisting of methyl, ethyl, and propyl.

* * * * *